United States Patent [19]

Markham

[11] Patent Number: 4,549,554
[45] Date of Patent: Oct. 29, 1985

[54] ASPIRATION BIOPSY DEVICE

[76] Inventor: Charles W. Markham, 667 Snug Island, Clearwater, Fla. 33515

[21] Appl. No.: 567,734

[22] Filed: Jan. 3, 1984

[51] Int. Cl.⁴ .............................................. A61B 10/00
[52] U.S. Cl. .................................................... 128/753
[58] Field of Search ............... 128/752, 753, 754, 763, 128/765, 766; 604/122, 124, 125, 187, 118, 236, 246, 247, 249; 417/490

[56] References Cited

U.S. PATENT DOCUMENTS

| | | | |
|---|---|---|---|
| 1,015,276 | 1/1912 | Rowse | 604/236 |
| 1,479,075 | 1/1924 | Johnson | 417/490 |
| 2,390,246 | 12/1945 | Folkman | 604/236 |
| 2,541,621 | 2/1951 | Thompson | 604/187 |
| 3,143,109 | 8/1964 | Gewertz | 128/766 |
| 4,073,288 | 2/1978 | Chapman | 128/766 |
| 4,326,541 | 4/1982 | Eckles | 128/766 |

Primary Examiner—Kyle L. Howell
Assistant Examiner—David Shay
Attorney, Agent, or Firm—Ronald E. Smith; Harold D. Shall

[57] ABSTRACT

An aspiration biopsy device in the form of a modified syringe having a pair of valves therein and a holding structure to hold the piston of the syringe in a desired vacuum creating location. In a first embodiment there is a stop cock type open-shut valve between the needle and the syringe body, a hole in the side of the syringe barrel intermediate the ends thereof and a spring, which when the stop cock is closed, biases the piston to a vacuum creating position with the piston head located between the hole and the needle. In a second embodiment, instead of the hole in the side of the barrel being intermediate the ends thereof, the hole is located near the needle mounting end of the barrel and an open-shut valve controls the opening and closing of such hole. In a third embodiment of this invention, instead of the spring of the first two embodiments, a physical stop arrangement is carried by the piston and the barrel to hold the piston in its vacuum creating position.

14 Claims, 4 Drawing Figures

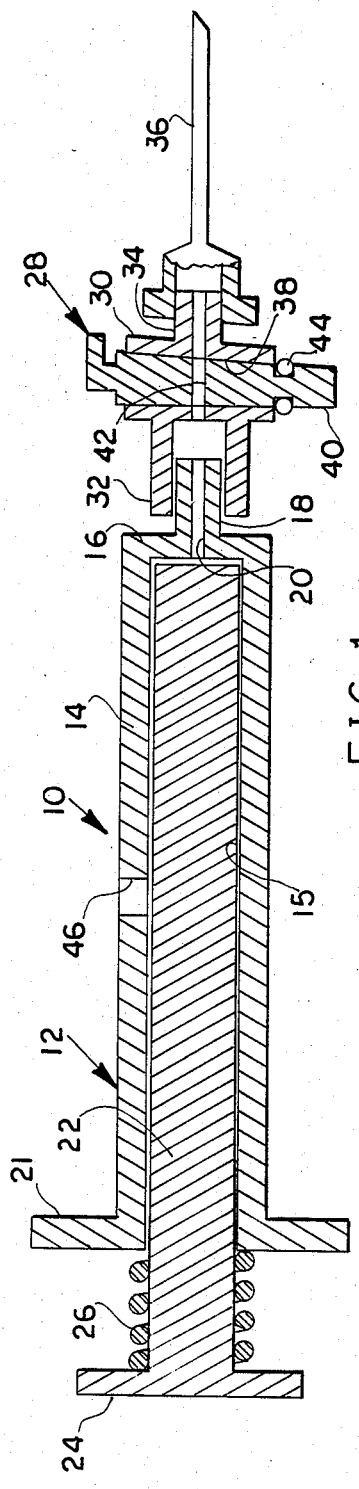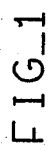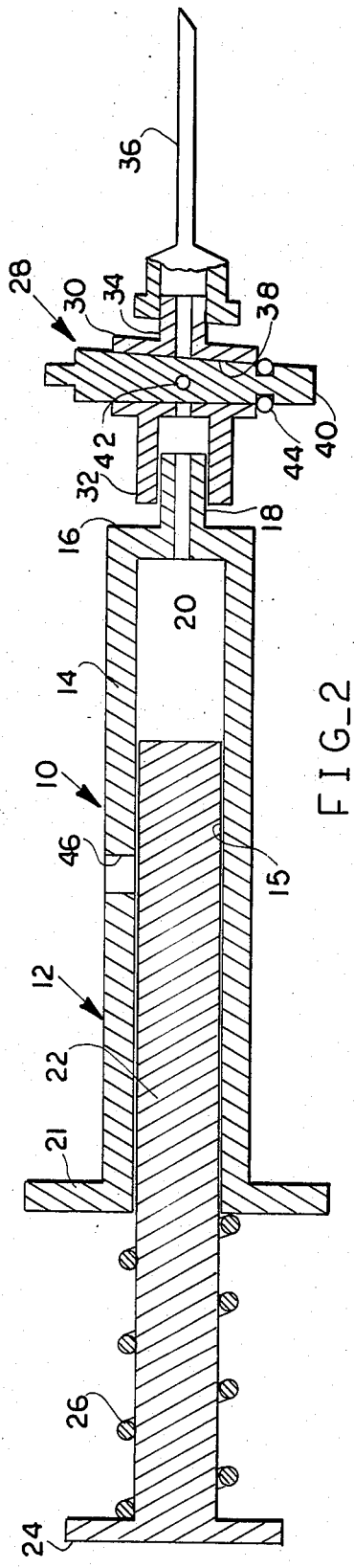

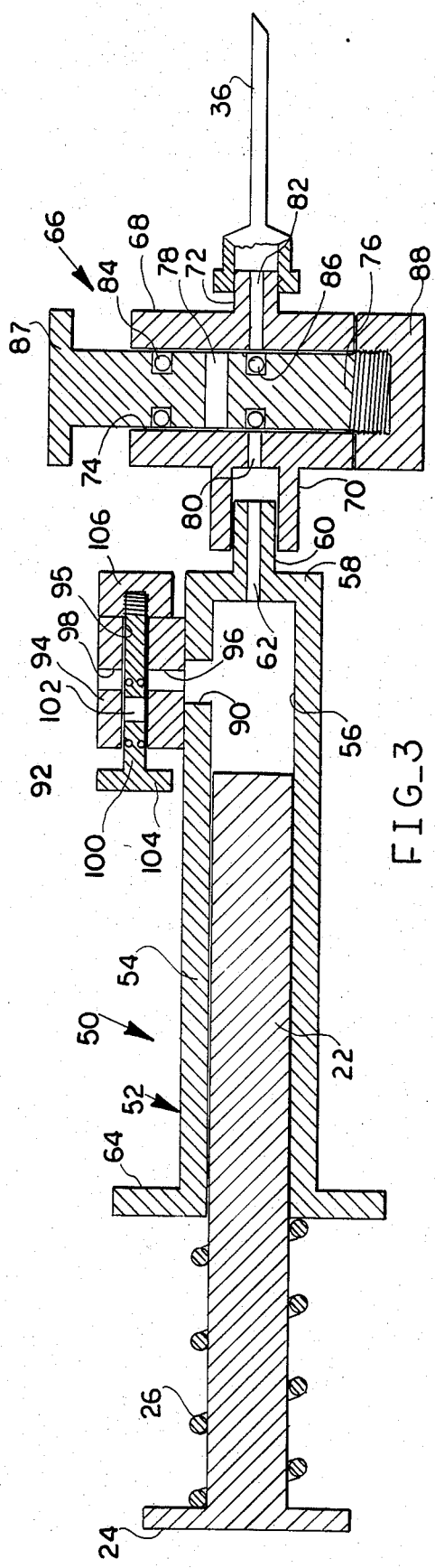
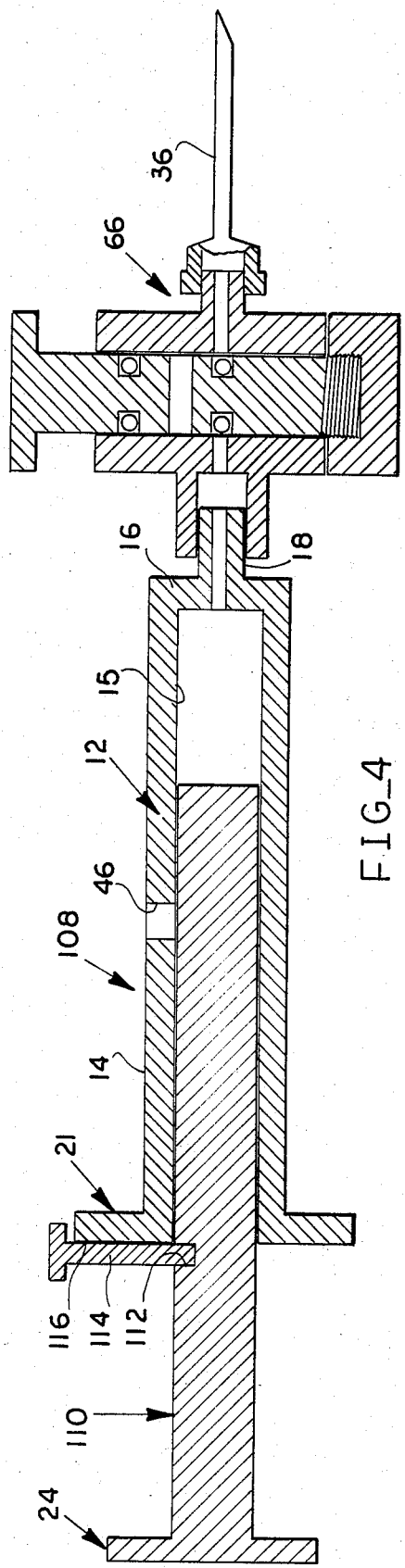

4,549,554

ASPIRATION BIOPSY DEVICE

BACKGROUND OF THE INVENTION

1. Field of the Invention

This invention relates generally to aspiration biopsy devices and in particular to such devices which are in the general configuration of a syringe with suitable valves thereon so that a controlled biopsy sample may be taken by one hand operation of the device.

2. Description of the Prior Art

Prior art aspiration biopsy devices include a standard syringe having a needle on the end thereof, wherein the physician operator first depresses the syringe piston completely inwardly, then inserts the needle into the suspect area, probes with the needle into the suspect tissue so that the needle shaves off a sample, and then while holding the barrel of the syringe with one hand, the operator pulls on the piston with the other hand to create a vacuum in the needle and draw some tissue sample into the needle. This is awkward in that two hands are necessary to manipulate the syringe, to draw the tissue sample, particularly when multiple samples are being taken at the same time and the second hand could be more appropriately used for purposes other than holding the syringe.

Another prior art device is like the above device, but includes a holding arrangement between the barrel of the syringe and the piston. In operation, the needle is inserted into the patient, the piston is withdrawn to the location of the holding device, which holds the piston in this location relative to the barrel, at which time the operator can manipulate the device with one hand. Since the needle is in the patient, a vacuum is created in the syringe and the physician can probe to shave off some sample which is drawn in the needle by the vacuum in the syringe. However, upon the syringe being withdrawn from the patient, the locked piston with its created vacuum, quickly draws the sample up the needle and into the barrel of the syringe where the sample is difficult to find and/or manipulate, unless the operator first uses his other hand to unlock the piston and control its movement so that the sample is not drawn into the barrel or ejected from the needle at a non-desired time.

A search of United States patents and foreign patents that was conducted prior to the filing of this disclosure located the following patents of interest in the general field of this invention:

U.S. Pat. Nos. 1,039,591; 2,472,116; 2,863,452 and 3,891,091.

None of the above patents is relevant to the instant invention as claimed. No representation is made or intended that the prior art search was complete or that no better art than that listed is available.

SUMMARY OF THE INVENTION

The present invention relates to an aspiration biopsy device in the form of a modified syringe which has two valves in it and also includes a device for controlling the position of the piston of the syringe during the probing and tissue gathering procedures so that the syringe can be operated by one hand.

The first valve is located between the barrel of the syringe and the needle and is an open-shut type valve such as a gate valve or a stopcock, which can be moved between its open and shut positions by one finger of the operator's hand while holding the syringe with that hand.

With the first valve closed, this invention includes an arrangement to hold the piston at an intermediate position in the barrel; the piston being moved to this position after the first valve (as well as the second valve) is closed so that a vacuum is created between the piston and the first valve. One such holding arrangement is a coil spring acting between the end of the barrel opposite the needle and the outer end of the piston to bias the piston outwardly against the reaction of the vacuum until a stable position is reached. A second such arrangement is a physical stop, which upon the piston being manually moved outwardly relative to the barrel to create a vacuum, the stop is engaged between the piston and the barrel to maintain the vacuum position until the stop is disconnected. The first valve may be opened and closed many times during the taking of a sample so that the needle may be moved to more than one location without losing the vacuum or withdrawing the sample.

The second valve is provided to relieve the vacuum after the needle has been withdrawn from the patient and to allow for the sample to be discharged through the needle. In a first embodiment, the valve comprises a hole in the barrel of the syringe at a position of the piston outwardly of the head thereof, so that the head of the piston blocks the hole from the needle, at such time as the piston is at its inward position or at its outward stable position as a result of the spring bias or the physical stop. To destroy the vacuum, the piston is merely manually moved outwardly in the barrel to allow air to enter the barrel through the hole in the barrel between the piston head and the barrel. In another embodiment, an open-shut valve is provided in the barrel at a location near the end of the barrel (between the head of the piston in its vacuum position and the end of the barrel). This open-shut valve is of the type easily operated by one finger of the operator's hand while holding the syringe with that hand. With the structure as described in this summary, a vacuum can be created in the barrel, the needle inserted into the patient, the first valve near the needle opened while the sample gathering is done, and this valve is then closed before the needle is withdrawn from the body. After withdrawal, the second valve is operated to eliminate the vacuum in the barrel, between the piston head and the first valve, the first valve is then opened, the second valve closed, and the piston moved toward the needle to discharge the sample.

It is an object of this invention to provide an aspiration biopsy device which is capable of one hand operation.

It is another object of this invention to provide such a device which gives the operator one hand control over the vacuum in the device so that sample dispersion is controlled.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 1 is a longitudinal sectional view of a first embodiment of this invention;

FIG. 2 is a longitudinal sectional view of the embodiment shown in FIG. 1 in a different operative position;

FIG. 3 is a longitudinal sectional view of a second embodiment of this invention; and FIG. 4 is a longitudinal sectional view of a third embodiment of this invention.

Similar reference numerals refer to similar parts throughout the several views of the drawings.

DETAILED DESCRIPTION OF THE PREFERRED EMBODIMENT

Referring now to the drawings, and more particularly to FIGS. 1 and 2, an aspiration biopsy device is shown generally at 10 and can be formed by modifying a commercially available syringe. A syringe barrel 12 has an elongated cylindrical tubular portion 14 surrounding a central cylindrical bore 15. At its right or needle mounting end, the tubular portion 14 is terminated by end wall 16, which end wall has a smaller cylindrical or needle mounting portion 18 extending therefrom, with the end wall and the mounting portion having a central opening 20 extending axially therethrough and confluent with the cylindrical bore 15. A left hand of the barrel has a narrow flange 21 extending peripherally therefrom.

A cylindrical syringe piston 22 is conventionally received in the bore 15 of the barrel 12 and is fitted therein to provide a telescoping air tight fit between the piston 22 and the barrel 12; however it should be noted that other methods of providing air tight fits between the piston 22 and barrel 12 are known in the art, as for example by using elastomeric sealing members (not shown) carried by the inner end of the piston and sealing engageable with the bore 15 of the barrel. The left end of the piston 22 terminates in a piston flange 24.

Surrounding the portion of the piston 22 outwardly of the barrel flange 21 is a coiled compression spring 26 which abuts the right or inner surface of the piston flange 24 and the left or outer surface of the barrel flange 21. As shown in FIG. 1, when the piston 22 is pushed inwardly of the barrel 12, the spring 26 is compressed and urges the piston outwardly of the barrel.

Mounted on the mounting portion 18 of the barrel 12 is an open-shut valve in the form of a conventional stopcock 28. The stopcock 28 has a central body portion 30 which has a cylindrical mounting portion 32 extending to the left therefrom and securely received in a sealing relationship on the mounting portion 18. The body portion 30 has a hollow cylindrical needle mounting portion 34 extending outwardly or to the right therefrom and mounted thereon is a needle 36 with a tapered point. The bores in the portions 34 and 32 are axially aligned.

The stopcock body 30 has a conventionally tapered bore 38 which conventionally receives a rotating valve member 40 which has a taper to sealingly match the taper in the bore 38. The bore 38 and valve member 40 are disposed transversely of the bores in the portions 32 and 34. An opening or bore 42 formed axially in the valve member 40 is adapted to be aligned with the bores in portions 32 and 34 in its open position as shown in FIG. 1, and, upon rotation of the valve member approximately ninety (90) degrees from its aligned position, to the position shown in FIG. 2, from its aligned position, the opening 42 will be completely blocked from the bores in the portions 32 and 34 and the valve 28 will be shut. An elastomeric ring 44 is conventionally received in a groove formed in the lower end of the rotating valve member 40 and abuttingly engages the lower end of the body portion 30 to position the valve member within the body portion; the ring 44 being removeable to disassemble and clean the stop cock 28.

A second valve is formed in the biopsy device 10. More particularly, an opening 46 is formed in the tubular portion 14 of the syringe barrel 12 at a location intermediate the end wall 16 and the barrel flange 21. The opening 46 is shown as being blocked by the piston 22 from the central opening 20 in the end wall 16 in the two (2) operative positions of the device shown in FIGS. 1 and 2. The opening 46 can be opened to be confluent with the central opening 20 at another operative position (not shown) of the piston 22 which will be hereinafter described.

The operation of the device of FIGS. 1 and 2 will now be described. With the open-shut valve 28 in its open position, as shown in FIG. 1, the piston 22 is completely depressed into the barrel 12 by the operator, thereby compressing the spring 26 and evacuating air from the cylindrical bore 15. With the piston depressed, the valve 28 is them moved to its closed position, as seen in FIG. 2 and the operator releases the piston 22. The spring 26 then biases the piston 22 outwardly of the barrel 12 to thereby create a partial vacuum between the inner or right hand of the piston 22 and the valve 28. The location of the opening 46 in the barrel 12 and the strength of the spring 26 are selected so that the vacuum within the barrel to the right of the piston will hold the piston in a position covering the opening 46. The strength of the spring 26 should also not be so great as to make it difficult for the operator to completely depress the piston.

The biopsy device 10 is now ready for single handed operation to obtain a sample from a patient. The operator holds the device 10 in one hand, inserts the needle into the suspect area of the patient, and then, utilizing one finger, for example the forefinger, of the holding hand rotates the rotating valve member 40 from its closed to its open position. The partial vacuum now extends to the end of the needle 36. The operator manipulates the needle in a well known manner to obtain tissue sample at the end of the needle 36 where the vacuum in the needle draws it at least partially into the needle, or at least the packing movement of the needle manipulation cooperates with the vacuum and forces sample at least part way up the needle. More than one location can be probed in the suspect area as long as the needle is not withdrawn from the patient; however, the needle can even be withdrawn without loss of vacuum or disturbance of the already gathered sample by closing the valve 28, withdrawing the needle, reinserting the needle, opening the valve 28 and gathering more sample. All this can be done with one hand operation.

When the sample gathering has been completed, the operator closes the valve 28, and withdraws the needle 36 from the patient. Since the valve 28 is closed, upon the needle being withdrawn from the patient, the partial vacuum between the end of the piston 22 and the valve 28 will not operate to draw the sample into the valve or even up into the tubular portion 14 or needle mounting portion 18.

Since the sample gathering is now complete, the operator now has the use of both hands to empty the device 10. To do so, he holds the barrel 12 with one hand, without covering the opening 46, and with the other hand draws the piston 22 farther out of the barrel 12 from its operative position shown in FIG. 2, to a position where the right end of the piston 22 is outwardly of the opening 46. Air can now enter to the right of piston 22 to relieve the vacuum within the barrel. The valve 28 is now opened and the piston 22 depressed. As the piston moves over and covers the opening 46, it becomes operative to create a pressure charge within the barrel 12 to the right of the piston 22, which pressure discharges the gathered sample from within the needle 36 so that the operator can view the same, for example on a slide under a microscope.

Referring now to the embodiment shown in FIG. 3, wherein like parts to those shown in FIGS. 1 and 2 will be referred to with like numbers, an aspirating biopsy device 50 includes a syringe barrel 52 having a tubular portion 54 surrounding a cylindrical central bore 56. At its right hand the tubular portion is terminated by an end wall 58 which has a smaller cylindrical needle mounting portion 60 extending therefrom with the end wall and the mounting portion having a central opening 62 extending axially therethrough and confluent with the bore 56. The left end of the barrel has a barrel flange 64 extending peripherally therefrom.

A cylindrical syringe portion 22 is conventionally received in the bore 56 of the barrel 54 and is fitted as described in the embodiment of FIGS. 1 and 2 above. The left end of the piston 22 terminates in a piston flange 24. A spring 26 surrounds the piston 22 outwardly of the barrel 54 and is compressed between the barrel flange 64 and the piston flange 24. When the piston 22 is pushed inwardly of the barrel 54, the spring 26 is compressed and urges the piston outwardly of the barrel.

Mounted on the mounting portion 60 is an open shut valve in the form of a gate valve 66. The gate valve 66 has a central body portion 68 which is elongated transversely of the mounting portion 60. The body portion 68 has a hollow cylindrical mounting portion 70 extending to the left therefrom and securedly received in a sealing relationship on the mounting portion 60. The body portion 68 has a hollow cylindrical needle mounting portion 72 extending outwardly to the right therefrom and mounted thereon is a needle 36 with a tapered point. The bores 80 and 82 in portions 70 and 72, respectively, are axially aligned and extend into a central bore 74 in the body portion 68.

The central bore 74 is square in cross section and closely receives for sliding movement a matching square valve stem 76 which has formed intermediate its ends an axially extending bore 78. With the valve stem in the position shown in FIG. 3, the bore 78 is not confluent with the bore 80 in the portion 70 or the bore 82 in the portion 72 and the valve is shut. When the stem is pushed downwardly, the bore 78 becomes confluent with the bores 80 and 82 and the valve is opened.

A slideable sealing material is received in a peripheral groove 84 formed in the valve stem 76 just above the bore 78 and slideable sealing material is received in a peripheral groove 86 formed in the valve stem 76 below the bore 78 at a location which blocks the bores 80 and 82 when the valve stem is in its upper, closed position; and is below the bores 80 and 82 when the stem is in its lower or open position. An upper knob 87 is formed on the upper end of the valve stem 76 and engages the valve body 68 when the stem is pushed downwardly, while a lower knob 88 is threaded on the lower end of the stem 76 and engages the valve body 68 when the stem is pushed upwardly.

An opening 90 is formed in the barrel 52 adjacent the right end thereof which opening is positioned between the end of the piston 22 and the end wall 58 when the piston 22 is biased outwardly by the spring 26 to its vacuum creating position. Bonded to the barrel 52 atop the opening 90 is a gate valve 92 of similar construction to the gate valve 66.

The gate valve 92 has a central body portion 94 which is elongated axially of the barrel 52 and has a central bore 95 which is square in cross section. A lower opening 96 is confluent with the bore 95 and the opening 90 while the upper opening 98 is confluent with the bore 95 and aligned with the lower opening 96. The central bore 95 closely receives for sliding movement a matching square valve stem 100 which has formed intermediate its ends a bore 102. When the stem is moved to the right, bore 102 becomes aligned with the openings 96 and 98, while when the stem is moved to the left, bore 102 is to the left of the openings 96 and 98. Sliding and sealing material is received in a pair of spaced grooves in the stem 100 in the same manner as with the stem 76 of the valve 66. On the left end of the stem 100 is a left knob 104 and threaded on the right end of the stem 100 is a right knob 106 which function the same way as the knobs 87 and 88 of the valve 66.

The operation of the device of FIG. 3 will now be explained. With the stem 76 of the valve 66 in its lower or open position, the piston 22 is depressed inwardly to the end wall 58 at which time the stem 76 of valve 66 is pushed upwardly to its closed position and the valve stem 100 of valve 92 is pushed to the left to its closed position. The piston 22 is now released and moves to the position shown in FIG. 3 wherein the spring 26 biases the piston to the left and a partial vacuum exists to the right of the piston. The device is now ready for one handed operation. The needle 36 can be inserted in the patient while the device is held in one hand, the valve 66 is opened with a finger of the holding hand, and a sample obtained as explained with respect to the embodiment of FIGS. 1 and 2. The valve stem 76 of valve 66 is now moved upwardly by the movement of a single finger of the holding hand to close valve 66 and the needle withdrawn from the patient. The valve stem 100 of the valve 92 is now pushed to the right by movement of a single finger of the holding hand, and the vacuum to the right of the piston 22 is ended by air entering through the aligned bores 98, 102 and 96 and the opening 90. The valve stem 100 of valve 92 is now pushed to the left by a single finger of the holding hand to close valve 92 and the valve stem 76 of the valve 66 is pushed downwardly by a single finger to open valve 66. At this time, the piston 22 can be pushed to the bottom of the barrel 52 to discharge the sample from the needle 36.

Referring now to the embodiment of this invention shown in FIG. 4, an open shut valve in the form of a gate valve 66, identical in configuration and operation to the gate valve 66 of FIG. 3, is utilized; however, an open shut valve like the stopcock 28 of FIGS. 1 and 2 could also be utilized.

The aspiration biopsy device 108 of this embodiment includes a barrel 12 identical to the barrel 12 of FIGS. 1 and 2, with a radially extending opening 46 formed in the tubular portion 12 of the barrel. A barrel 12 has an end wall 16 with a cylindrical or needle mounting portion 18 extending conventional therefrom and mounted thereon is the gate valve 66.

A syringe piston 110 is conventionally received in the bore 15 of the barrel 12 and fitted to provide a telescoping air tight fit. Means are provided for holding the piston at an intermediate position in the barrel 12. More particularly, the piston 110 has a radially extending opening 112 formed therein at a location intermediate its ends; the opening being dimensioned so as to securedly receive a lock pin 114 therein and is positioned axially along the length of the piston 110 so that with the valve 66 closed and the piston moved to the desired vacuum position, the pin 114 can be positioned in the opening 112 and will abut the outer or left face 116 of the flange 21 on the barrel 12 to hold the piston in its vacuum position.

In operation of the embodiment of FIG. 4, with the lock pin 114 removed and the valve 66 open, the piston 110 is forced to its inward position in the barrel 12. The valve 66 is then closed, and the piston moved to its vacuum position and the lock pin 114 inserted into the opening 112. The aspiration device 108 is now ready to be manipulated to gather a sample by one hand operation. The operator inserts the needle into the patient and into the suspect area. A single finger on the holding hand opens the valve 66 while the needle end is used to shave off some suspect tissue which is drawn into the needle by the vacuum therein. When the sample gathering is done, the valve 66 is closed by one finger manipulation of the operating hand, and the sample withdrawn from the patient. The piston 110 is now moved outwardly of the barrel 12 until the opening 46 is uncovered to vent air to the vacuum within the barrel. The pin 114 is now withdrawn from the opening 112, the valve 66 is opened, and the piston 110 depressed into the barrel 12. Upon the piston 110 covering the opening 46, pressure can be generated to the right of the piston 110 to allow the further movement of the piston 110 to expel the sample from the needle 36 where it can be inspected by the operator.

Although the description relates to presently preferred embodiments, numerous modifications may be made without departing from the spirit of the invention as defined in the claims.

It will thus be seen that the objects set forth above, and those made apparent by the preceding description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:

1. An aspiration biopsy device of modified syringe construction, which syringe has a barrel, an air tight telescopically mounted piston therein, a needle mounted at the end of the barrel opposite its needle-mounting end, wherein the improvement comprises a holding means for holding said piston in a vacuum creating position intermediate the ends of the barrel, first open shut valve means for selectively opening and closing said barrel from a needle mounted on said device, and a second open shut valve means for selectively venting any vacuum which might exist between the inner end of said piston and said first valve means, and said holding means comprising an operator-controlled selectively engageable and disengageable physical stop means acting between said piston and said barrel.

2. An aspiration biopsy device of modified syringe construction, which syringe has a barrel, an air tight telescopically mounted piston therein, a needle mounted at the end of the barrel opposite its piston-receiving end, and which piston is operative to discharge or draw gaseous or liquid fluids out of or into said barrel, wherein the improvement comprises:
holding means in the form of a compression spring reacting between said barrel and said piston for holding said piston in a vacuum creating position intermediate the ends of the barrel, first operator-controlled open shut valve means for selectively opening and closing said barrel from a needle mounted on said device, and a second open shut valve means for selectively venting any vacuum which might exist between the inner end of said piston and said first valve means.

3. A device according to claim 1, wherein said compression spring comprises a coil compression spring received around the axially outer end of said piston.

4. A device according to claim 2 wherein said barrel has a cylindrical portion extending axially from the end thereof opposite the piston receiving end, which cylindrical portion conventionally mounts a needle thereon, said first open shut valve is mounted on said cylindrical portion, and said first open shut valve includes means thereon for mounting a needle.

5. A device according to claim 2 wherein said second valve means comprises an opening in said barrel wall, and the head of said piston in its vacuum created intermediate position separates said opening from said first valve means.

6. A device according to claim 5 wherein said holding means can be overridden and said piston means is movable axially outwardly to allow said opening to be confluent with said first valve means.

7. A device according to claim 2 wherein said second valve means comprises an opening in the barrel wall disposed between the head of said piston separating said head from said first valve means when said piston is in its vacuum creating position, said second valve means also includes an open shut valve means for selectively opening and closing said opening.

8. An aspiration biopsy device comprising a cylindrical barrel having an inner and outer end, a needle mounted on said inner end, a piston sealingly and telescopically received in the barrel from the outer end thereof with said piston projecting out of said barrel when in its fully inward position, holding means for holding said piston in a vacuum creating position with the head thereof intermediate the ends of said barrel, an opening formed in the inner end of said barrel, first operator-controlled open shut valve means including means mounting the same on said barrel whereby said first valve means is selectively operable to open and shut the opening in the inner end in said barrel, and second valve means for selectively venting any vacuum which might exist between the inner end of said piston and said first valve means.

9. A device according to claim 8 wherein said holding means comprises a compression spring means reacting between said barrel and said piston for biasing said piston outwardly of said barrel.

10. A device according to claim 8 wherein said holding means comprises a selectively engageable and disengageable physical stop means acting between said piston and said barrel.

11. A device according to claim 8 wherein said barrel has a cylindrical portion extending axially from the end thereof opposite the piston receiving end, said first valve means is an open shut valve and is mounted on said cylindrical portion, and said first open shut valve includes means thereon mounting said needle.

12. A device according to claim 8 wherein said second valve means comprises an opening in the barrel wall disposed between the head of said piston from said first valve means when said piston is in its vacuum creating position, said second valve means also includes an open shut valve means for selectively opening and closing said opening.

13. A device according to claim 8 wherein said second valve means comprises an opening in said barrel wall and the head of said piston in its vacuum creating intermediate position separates said opening from said first valve means.

14. A device according to claim 13 wherein said holding means can be overridden and said piston means is movable axially outwardly to allow said opening to become confluent with said first valve means.

* * * * *